US00PP35362P3

(12) United States Plant Patent
Bull

(10) Patent No.: US PP35,362 P3
(45) Date of Patent: Aug. 29, 2023

(54) ***RUDBECKIA* PLANT NAMED 'BULLRUDIHIR 117'**

(50) Latin Name: ***Rudbeckia hirta* L.**
Varietal Denomination: BullRudihir 117

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 17/974,812

(22) Filed: Oct. 27, 2022

(65) Prior Publication Data

US 2023/0140852 P1 May 4, 2023

Related U.S. Application Data

(60) Provisional application No. 63/360,790, filed on Oct. 28, 2021.

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 6/14; A01H 5/02
See application file for complete search history.

*Primary Examiner* — Keith O. Robinson
(74) *Attorney, Agent, or Firm* — The Webb Law Firm

(57) ABSTRACT

A new and distinct variety of *Rudbeckia* plant having a compact growth habit and semi-double, rich yellow and brown blooms with a dark brown center.

1 Drawing Sheet

Botanical classification: *Rudbeckia hirta* L.
Varietal denomination: 'BullRudihir 117'.

BACKGROUND OF THE INVENTION

The present invention comprises a new and distinct cultivar of *Rudbeckia* plant known by the varietal name 'BullRudihir 117'. The new variety was discovered in August of 2019 in Gönnebek, Germany as the result of a planned breeding program with the purposes of providing *Rudbeckia* plants with improved growth, more uniformity, a compact growth habit, better branching, attractive foliage, large flowers, unique flower colors, and double flowers. The new variety is the result of a cross between an unpatented *Rudbeckia hirta* L. variety having an internal breeder's reference of "BR 16-2018" (female parent) and an unpatented *Rudbeckia hirta* L. variety having an internal breeder's reference of "BR 19-2018" (male parent) from the breeder's own collection. The new variety was first asexually reproduced via in-vitro tissue culture cuttings in Gönnebek, Germany in September of 2019. The new variety is similar to its parental varieties in botanical classification, but exhibits semi-double, bicolored flowers, increased branching, and more attractive foliage than both of its parental varieties. Further, 'BullRudihir 117' exhibits a different colored flower center than its female parent and a more compact growth habit that distinguishes it from its male parent.

When 'BullRudihir 117' is compared to *Rudbeckia hirta* L. variety named 'Goldilocks' (unpatented), 'BullRudihir 117' is similar to 'Goldilocks' in botanical classification, but 'BullRudihir 117' exhibits semi-double, bicolored flowers, improved plant quality, more uniform growth with increased self-branching, and more attractive foliage than 'Goldilocks'. Further, the following characteristics distinguish 'BullRudihir 117' when generally compared to other *Rudbeckia* varieties known to the breeder:

Large, bicolored flowers with a brown center;
Good self-branching;
An upright, compact, and uniform growth habit;
Healthy, green foliage;
Long bloom time;
Ease of growth;
Semi-double flowers; and
Unique flower color combination.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawing illustrates the new variety at 18 weeks of age, with the color being as nearly true as is possible with color illustrations of this type:

FIG. 1 shows an entire plant of the new variety.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 21 cm (4 liter) pots under normal field production conditions. The color readings and measurements were observed outdoors under natural light on 18 week old plants in Gönnebek, Germany. Color references are primarily to The 2015 R.H.S. Colour Chart of The Royal Horticultural Society of London, Sixth Edition, except where terms of ordinary significance are used.

PLANT

Time to initiate roots: About 7-10 days at approximately 18° C.

Time to develop roots: About 35-38 days at approximately 16-18° C.

Time to produce a finished flowering plant from a rooted cutting: About 11-14 weeks in a 21 cm container.

Rooting habit: Exhibits numerous roots of medium thickness that are freely branching and healthy in appearance.

Plant height: 50.0-65.0 cm.

Plant width: 35.0-40.0 cm.

Vigor: High, with an upright, compact, and uniform growth habit.

Disease/pest resistance: Nothing unusual noted to date.

Temperature tolerance: From −3 to +40° C.

Drought tolerance: Average.

Branching habit: Exhibits one dominant strong branch with several lateral side branches. The lateral branches are upright, forming an attractive habit.

Branches (flowering stems):

*Number per plant.*—10-20.
*Length.*—10.0-45.0 cm.
*Diameter.*—5.0-10.0 mm.
*Internode length.*—2.0-10.0 cm.
*Angle.*—Upright and outward.
*Strength.*—Strong.
*Texture.*—Pubescence present.
*Color.*—Close to Yellow-Green Group RHS 144A to 144B.

Foliage:

*Arrangement.*—Single.
*Leaf.*—Length: 6.0-25.0 cm. Width: 1.5-8.0 cm. Shape: Oblanceolate. Apex: Acuminate. Base: Attenuate to acute. Margin: Dentate and undulate. Texture: Upper surface: Rough, with pubescence present. Lower surface: Rough, with pubescence present. Color: Young leaves: Upper surface: Close to Green Group RHS 137B. Lower surface: Close to Green Group RHS 137C. Mature leaves: Upper surface: Close to Green Group RHS 137B to 137C. Lower surface: Close to Green Group RHS 137D. Petiole: None present. Veins: Venation type: Pinnate. Color: Upper surface: Close to Yellow-Green Group RHS 145C. Lower surface: Close to Yellow-Green Group RHS 145A.

INFLORESCENCE

Bud:

*Diameter.*—3.0-5.0 cm.
*Length.*—2.0-6.0 cm.
*Color.*—Close to Yellow-Green Group RHS 151A.

Appearance: Elliptic-shaped ray florets and tubular-shaped disc florets.

Natural flowering season: Flowering occurs from June-October in Gönnebek, Germany, beginning approximately 10-12 weeks after planting.

Average number of inflorescences per plant: 10-30.

Average number of inflorescences per branch: 1-5.

Disc and ray floret arrangement: Disc florets are arranged in the middle of the receptacle of the composite, semi-double, freely flowering plant, with ray florets extending outwardly therefrom.

Lastingness of an inflorescence on the plant: 5-6 weeks.

Lastingness of an inflorescence off the plant: 5-6 weeks.

Fragrance: Very light and sweet.

Inflorescence:

*Diameter.*—10.0-17.0 cm.
*Height (depth).*—2.0-4.0 cm.
*Diameter of disc.*—2.5-6.0 cm.
*Receptacle height.*—1.0-1.5 cm.
*Receptacle diameter.*—4.0-8.0 cm.

Ray florets:

*Number per inflorescence.*—25-44.
*Arrangement.*—In three to five whorls.
*Length.*—4.0-8.0 cm.
*Width.*—1.5-3.0 cm.
*Shape.*—Elliptical.
*Apex.*—Emarginate.
*Base.*—Acute.
*Margin.*—Entire.
*Texture.*—Upper surface: Smooth and glabrous. Lower surface: Rough.
*Color.*—When opening: Upper surface: Close to Yellow-Orange Group RHS 17B, with close to Red Group RHS 47A coloration from the base to the midpoint. Lower surface: Close to Yellow-Orange Group RHS 15B. At maturity: Upper surface: Close to Yellow-Orange Group RHS 17B, with close to Orange-Red Group RHS 34A coloration from the base to the midpoint. Lower surface: Close to Yellow-Orange Group RHS 15B, with a shine of close to Orange-Red Group RHS 34C. Ground color description: Close to Yellow-Orange Group RHS 17B, with close to Orange-Red Group RHS 34A coloration from the base to the midpoint.
*Venation.*—Appearance: Parallel. Color: Upper surface: Same color as the florets. Lower surface: Same color as the florets.

Disc florets:

*Number per inflorescence.*—Numerous; too many to quantify.
*Arrangement.*—In the center of receptacle.
*Length.*—5.0-10.0 mm.
*Width.*—About 1.0 mm.
*Shape.*—Tubular.
*Apex.*—Five-pointed.
*Color.*—Immature: Close to Brown Group RHS 200A. At maturity: Close to Brown Group RHS 200A.

Phyllaries:

*Number per inflorescence.*—30-40.
*Arrangement.*—In three whorls.
*Length.*—1.0-3.0 cm.
*Width.*—3.0-8.0 mm.
*Shape.*—Lanceolate.
*Apex.*—Elongated oval.
*Base.*—Fused.
*Margin.*—Undulate.
*Texture.*—Upper surface: Rough, with pubescence present. Lower surface: Rough, with pubescence present.
*Color.*—Immature: Upper surface: Close to Green Group RHS 138A. Lower surface: Close to Green Group RHS 138B. At maturity: Upper surface: Close to Green Group RHS 138A. Lower surface: Close to Green Group RHS 138B.

Reproductive organs:

Androecium:

*Presence*.—On disc and ray florets.

*Number* (*per floret*).—Numerous; too many to quantify.

*Filament length*.—1.0-2.0 mm.

*Filament color*.—Close to Brown Group RHS 200A.

*Anther*.—Shape: Oval. Length: 1.0 mm. Color: Close to Brown Group RHS 200A.

*Pollen*.—Color: Close to Yellow-Orange Group RHS 16A. Amount: Plentiful — too much to quantify.

Gynoecium:

*Presence*.—On disc florets.

*Pistil length*.—About 2.0 mm.

*Stigma*.—Shape: Two-parted. Color: Close to Brown Group RHS 200A.

*Style*.—Length: 1.0-2.0 mm. Color: Close to Brown Group RHS 200A.

Seeds:

*Overall size*.—Approximately 2.0 mm.

*Color*.—Close to Black Group RHS 202A.

I claim:

1. A new and distinct variety of *Rudbeckia* plant named 'BullRudihir 117', as is herein illustrated and described.

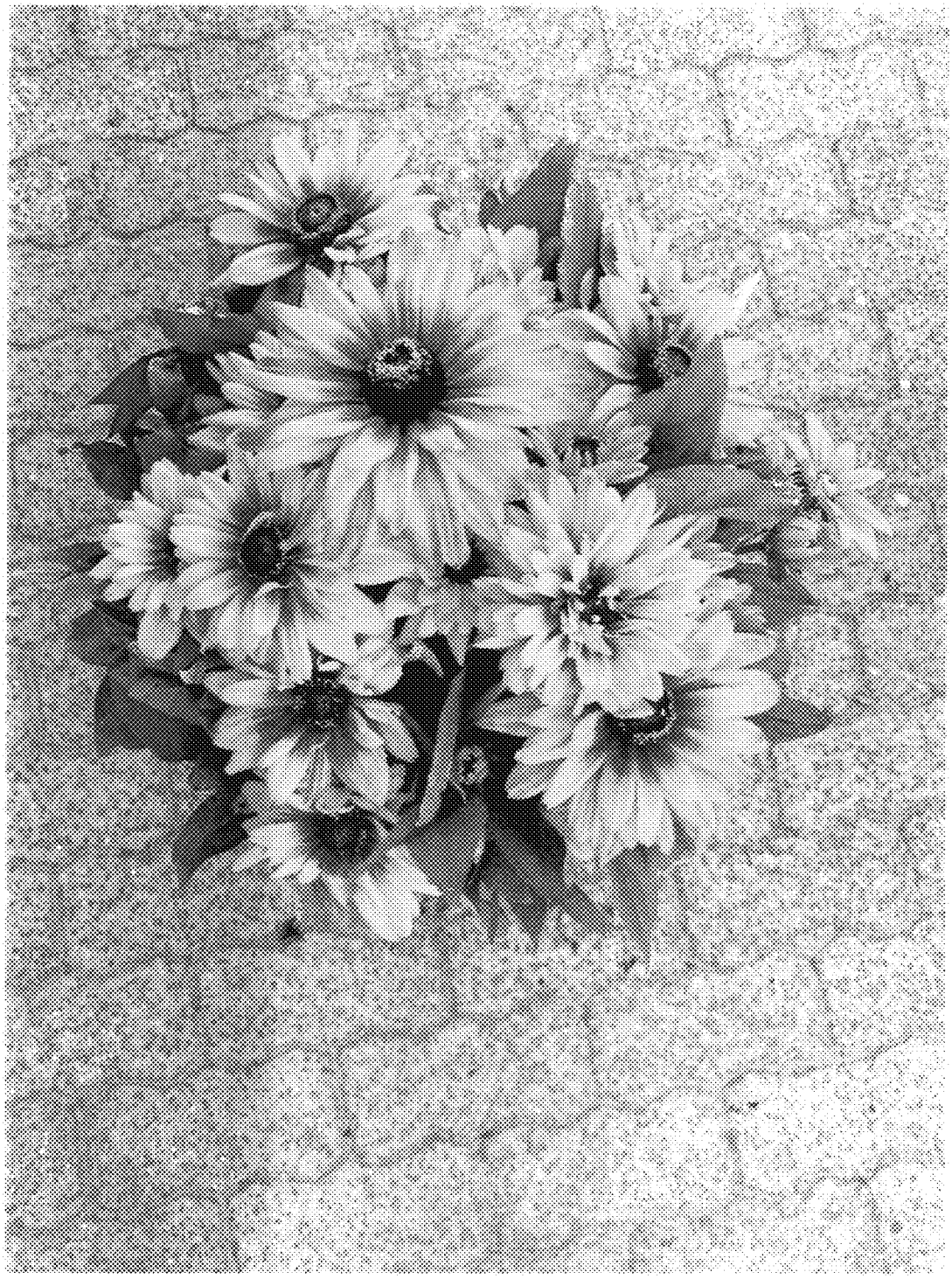

* * * * *